US00PP16839P2

(12) United States Plant Patent
Vanderhaegen

(10) Patent No.: US PP16,839 P2
(45) Date of Patent: Jul. 18, 2006

(54) ***RHODODENDRON* PLANT NAMED 'CARMEN'**

(50) Latin Name: ***Rhododendron simsii*×*Rhododendron obtusum***
Varietal Denomination: Carmen

(75) Inventor: Johan Vanderhaegen, Kruishoutem (BE)

(73) Assignee: Hortibreed BV, Lochristi (BE)

( * ) Notice: Subject to any disclaimer, the term of this patent is extended or adjusted under 35 U.S.C. 154(b) by 49 days.

(21) Appl. No.: 11/082,722

(22) Filed: Mar. 17, 2005

(51) Int. Cl.
*A01H 5/00* (2006.01)

(52) U.S. Cl. ..... Plt./239

(58) Field of Classification Search ..... Plt./239
See application file for complete search history.

*Primary Examiner*—Anne Marie Grunberg
*Assistant Examiner*—Georgia Helmer
(74) *Attorney, Agent, or Firm*—Mark P. Bourgeois

(57) ABSTRACT

A new cultivar of *Rhododendron* plant named 'Carmen' that is characterized by vigorous growth, good leaf retention, double light pink flowers, a flower life of 3 to 4 weeks and winter hardiness to −10 degrees Centigrade.

1 Drawing Sheet

Botanical classification: *Rhododendron simsii*×*Rhododendron obtusum.*
Variety denomination: 'Carmen'.

BACKGROUND OF THE INVENTION

The present invention relates to a new and distinct cultivar of *Rhododendron* plant botanically known as *Rhododendron simsii* and hereinafter referred to by the cultivar name 'Carmen'.

'Carmen' is a hybrid that originated from the induced hybridization of the female or seed parent *Rhododendron simsii* 'Helmut Vogel' (not patented) and the male or pollen parent *Rhododendron obtusum* 'Rose Bud' (not patented). The cultivar 'Carmen' was selected by the inventor in 1994 as a single plant within the progeny of the stated cross in a cultivated area of Kruishoutem, Belgium.

Asexual reproduction of the new cultivar 'Carmen' by cuttings was first performed in 1994 in Kruishoutem, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Rhododendron* cultivar 'Carmen'. These traits in combination distinguish 'Carmen' as a new and distinct cultivar apart from all other existing varieties of *Rhododendron* known to the inventor.

1. *Rhododendron* 'Carmen' exhibits vigorous growth.
2. *Rhododendron* 'Carmen' exhibits good leaf retention.
3. *Rhododendron* 'Carmen' exhibits double light pink flowers.
4. *Rhododendron* 'Carmen' exhibits a flower life of 3 to 4 weeks.
5. *Rhododendron* 'Carmen' exhibits winter hardiness to −10 degrees Centigrade.

The new cultivar 'Carmen' is distinguishable from the female parent *Rhododendron* 'Helmut Vogel' by the following characteristics:

1. 'Carmen' has better winter hardiness to −10 degrees Centigrade.
2. 'Carmen' has smaller flowers.

The new cultivar 'Carmen' is distinguishable from the male parent *Rhododendron* 'Rose Bud' by the following characteristics:

1. 'Carmen' has good leaf retention. The leaves of the male parent are subject to leaf drop.
2. 'Carmen' has a lighter flower color.
3. 'Carmen' has smaller flowers.

The closest comparison cultivar is the male parent *Rhododendron* 'Rose Bud'.

BRIEF DESCRIPTION OF THE DRAWING

The accompanying photograph illustrates the distinguishing traits of *Rhododendron* 'Carmen'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Rhododendron* cultivar named 'Carmen'. Data was collected in Kruishoutem, Belgium from 24 month old glass greenhouse grown plants in 14 cm. containers. The time of year was Winter and the average daytime temperature was 20° Centigrade during the Summer and 4° Centigrade during the Winter. The average nighttime temperature was 15° Centigrade during the Summer and 4° Centigrade during the Winter. The light level was natural outdoor light and there were no photoperiodic treatments. Pinching was performed between the end of April and the middle of June. Osmocote was applied at the rate of 1 gram per liter. Color determinations are in accordance with The Royal Horticultural Society Colour Chart 2001 edition, except where general color terms of ordinary dictionary significance are used. The growing requirements are similar to the species. 'Carmen' has not been tested under all possible conditions and phenotypic differences may be observed with variations in environmental, climatic, and cultural conditions, however, without any variance in genotype.

Botanical classification: *Rhododendron simsii*× *Rhododendron obtusum* 'Carmen'.
Use: Ornamental Perennial.
Parentage: 'Carmen' is a hybrid that resulted from the induced hybridization of the following plants:
Female or seed parent *Rhododendron simsii* 'Helmut Vogel'.
Male or pollen parent *Rhododendron obtusum* 'Rose Bud'.
Vigor: Moderate.
Growth rate: Approximately 8 to 15 cm. per year.
Growth habit: Broad upright, densely branched.
Plant shape: Flattened globose.
Suitable container size: 1.0 liter container.
Height: Average 19.0 cm. in height.
Width: Average 27.0 cm. in width.
Hardiness: −10 degrees Centigrade.
Propagation: Cuttings.
Time to initiate roots: Approximately 30 days to produce roots on an initial cutting.
Time to produce a rooted cutting or liner: Approximately 60 days.
Root system: Fine and fibrous.
Stem:
*Branching habit*.—Freely branching.
*Average number of lateral branches*.—6.
*Pinching*.—Yes.
*Lateral branch diameter*.—2.5 mm. in diameter.
*Lateral branch length*.—11.0 cm. in length.
*Lateral branch strength*.—Moderately strong.
*Stem color*.—144B, older stems 200D.
*Pubescence*.—Dense, length 1.5 mm, color 175C to 175D.
*Internode length*.—8 mm. between nodes.
*Shape*.—Round.
*Surface*.—Dull.
*Stem strength*.—Moderately strong.
Foliage:
*Texture*.—Dull, slightly leathery.
*Leaf arrangement*.—Alternate, clustered towards the top of the stems.
*Compound or single*.—Single.
*Quantity of leaves per lateral branch*.—22.
*Leaf shape*.—Elliptic.
*Leaf apex*.—Acute.
*Leaf base*.—Acute.
*Leaf length*.—4.8 cm. in length.
*Leaf width*.—2.0 cm. in width.
*Pubescence*.—Slight, both sides, length 1 mm, color gray-orange N175C to N175D.
*Leaf margin*.—Entire.
*Vein pattern*.—Pinnate.
*Young leaf color* (*upper surface*).—137C.
*Young leaf color* (*lower surface*).—138B.
*Mature leaf color* (*upper surface*).—136B.
*Mature leaf color* (*lower surface*).—138A.
*Vein color* (*lower surface*).—143C.
*Vein color* (*upper surface*).—143B.
*Leaf attachment*.—Petiolate.
*Petiole dimensions*.—9 mm. in length and 2 mm. in diameter.
*Petiole color*.—145A.
*Durability of foliage to stress*.—High.
Flower:
*Flower arrangement*.—Terminal clusters.
*Inflorescence type*.—Double.
*Inflorescence dimensions*.—7.5 cm. in diameter and 4.0 cm. in height.
*Flowering habit*.—Continuously once a year.
*Quantity of flowers per lateral stem*.—Approximately 5.
*Quantity of flower buds per lateral stem*.—Approximately 5.
*Quantity of flowers and buds per plant*.—Approximately 155.
*Flowering season*.—Spring.
*Time to flower or response time*.—10.0 months.
*Rate of flower opening*.—After the first flower of a cluster has opened, all flowers of that cluster will open in approximately 14 days.
*Fragrance*.—None.
*Self-cleaning or persistent*.—Self-cleaning.
*Flower bud length*.—9 mm. in length.
*Flower bud diameter*.—7 mm. in diameter.
*Flower bud shape*.—Ovate.
*Bud color*.—151D.
*Rate of bud opening*.—10 days.
*Flower aspect*.—Upright to outward.
*Flower shape*.—Funnelform.
*Flower dimensions*.—Average 7.5 cm. in diameter and 5.0 cm. in height.
*Flower longevity*.—Lasts approximately 24 to 30 days on plant.
*Petal appearance*.—Dull, slight velvety.
*Petal texture*.—Glabrous.
*Petal arrangement*.—Fused into a funnelform shape.
*Number of petals*.—Five in number.
*Petals fused or unfused*.—Lower ¼ of petals are fused.
*Petal shape*.—Irregular obovate.
*Petal margin*.—Entire.
*Petal apex*.—Rounded.
*Petal dimensions*.—Average 2.3 cm. in length and 1.5 cm. in width.
*Petal color when opening* (*upper side*).—65A, base 144D.
*Petal color when opening* (*under side*).—68B, changing to 68C to 68D towards the base, base 144D.
*Petal color when fully opened* (*upper side*).—65A, base 144D.
*Petal color when fully opened* (*under side*).—68B, changing to 68C to 68D towards the base, base 144D.
*Petal color fading to*.—Not fading.
*Petaloid appearance*.—Dull, slight velvety.
*Petaloid arrangement*.—Rotate, in the center of the flower.
*Number of petaloids*.—Average Five in number.
*Petaloid shape*.—Obovate.
*Petaloid margin*.—Entire.
*Petaloid apex*.—Rounded.
*Petaloid dimensions*.—Average 2.3 cm. in length and 1.2 cm. in width.
*Petaloid color when opening* (*both sides*).—65A to 68B, lighter toward the base 68C to 68D.

*Petaloid color when fully opened* (*both sides*).—65A to 68B, lighter toward the base 68C to 68D.

Calyx:

*Calyx shape*.—Campanulate.

*Calyx dimensions*.—7.0 mm. in length and 1.1 cm. in diameter.

Sepals:

*Sepal appearance*.—Dull, pubescent.

*Sepal arrangement*.—Campanulate.

*Number of sepals*.—Five in number.

*Sepals fused or unfused*.—Lower 50% fused.

*Sepal shape*.—Ovate.

*Sepal margin*.—Entire.

*Sepal apex*.—Acute.

*Sepal dimensions*.—Average 7.0 mm. in length and 4.0 mm. in width.

*Sepal color when opening* (*both sides*).—144A.

*Sepal color when fully opened* (*both sides*).—144A.

Bracts:

*Number of bracts*.—5 in number.

*Bract dimensions*.—1.2 cm. in length and 7 mm. in width.

*Bract shape*.—Ovate.

*Bract apex*.—Acute.

*Bract pubescence*.—Sparsely covered on under side, 1.5 mm in length, color 175C to 175D.

*Bract color* (*both sides*).—144A.

Reproduction organs:

*Stamen number*.—1.

*Anther shape*.—Dorsifixed, oval, not fully developed.

*Amount of pollen*.—None.

*Pistil number*.—1, not fully developed.

*Pistil dimensions*.—1.8 cm. in length.

*Stigma shape*.—Club shaped, flattened at the top.

*Stigma color*.—144B.

*Style length*.—1.75 mm.

*Style color*.—145C with a base 145A.

*Ovary color*.—138A to 138B.

Seed: Seed production has not been observed.

Disease and pest resistance: Plants of the new *Rhododendron* have not been observed for disease or pest resistance.

It is claimed:

1. A new and distinct variety of *Rhododendron* plant named 'Carmen' as described and illustrated.

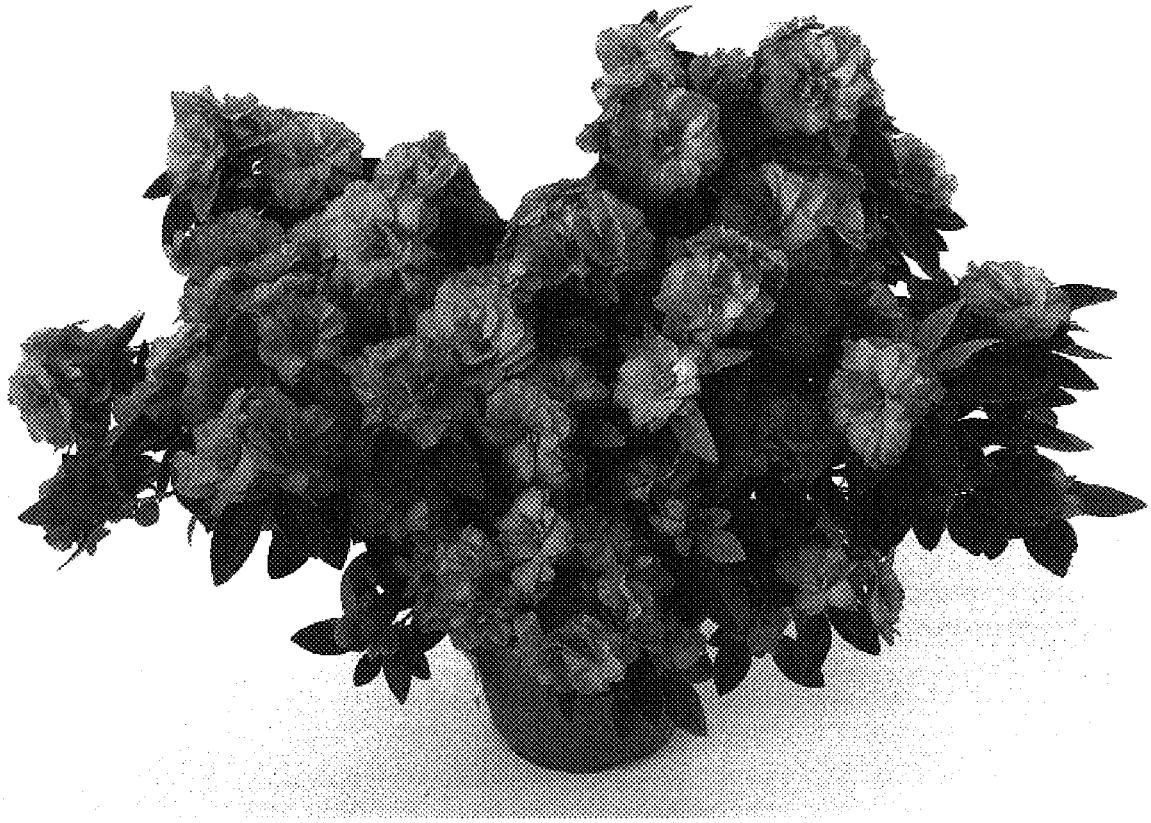

* * * * *